US00RE46496E

(19) United States
(12) Reissued Patent
Lara

(10) Patent Number: US RE46,496 E
(45) Date of Reissued Patent: Aug. 1, 2017

(54) METFORMIN GLYCINATE FOR BLOOD GLUCOSE CONTROL

(71) Applicant: Laboratorios Silanes S.A. de C.V., México, DF (MX)

(72) Inventor: Jose Manuel Francisco Ochoa Lara, Jardines del Pedregal (MX)

(73) Assignee: Laboratorios Silanes S.A. de C.V., México (MX)

(21) Appl. No.: 15/135,018

(22) Filed: Apr. 21, 2016

Related U.S. Patent Documents

Reissue of:
(64) Patent No.: 8,703,183
Issued: Apr. 22, 2014
Appl. No.: 12/928,985
Filed: Dec. 24, 2010

U.S. Applications:
(63) Continuation-in-part of application No. PCT/IB2008/002665, filed on Jun. 26, 2008.

(51) Int. Cl.

| | |
|---|---|
| ***A61K 9/20*** | (2006.01) |
| ***A61K 31/27*** | (2006.01) |
| ***C07C 61/08*** | (2006.01) |
| ***C07C 229/00*** | (2006.01) |
| ***C07C 251/00*** | (2006.01) |
| ***A61K 31/15*** | (2006.01) |
| ***A61K 31/131*** | (2006.01) |
| ***A61K 31/198*** | (2006.01) |
| ***C07C 279/26*** | (2006.01) |
| ***C07C 229/08*** | (2006.01) |

(52) U.S. Cl.
CPC ..... *C07C 279/26* (2013.01); *C07C 229/08* (2013.01)

(58) Field of Classification Search
CPC ..... C07C 279/26; C07C 229/08
USPC ..... 424/451
See application file for complete search history.

(56) References Cited

U.S. PATENT DOCUMENTS

| | | | | |
|---|---|---|---|---|
| 6,329,545 | B1 * | 12/2001 | Larsen et al. | 562/439 |
| 6,936,275 | B2 | 8/2005 | Fassihi et al. | |
| 7,229,642 | B2 | 6/2007 | Fassihi et al. | |
| 2003/0220301 | A1 * | 11/2003 | Lal et al. | 514/101 |
| 2008/0031964 | A1 | 2/2008 | Messadek | |

FOREIGN PATENT DOCUMENTS

| | | | | |
|---|---|---|---|---|
| GB | 1473256 | A * | 10/1974 | |
| GB | 1473256 | A | 5/1977 | |
| WO | WO 2005/065675 | A | 7/2005 | |
| WO | WO 2006/086856 | A | 8/2006 | |
| WO | WO2009/014457 | A1 * | 12/2009 | C07C 279/26 |
| WO | WO 2009/144527 | A1 | 12/2009 | |

OTHER PUBLICATIONS

Garza-Ocanas et al., "Pharnacokinetics and Gastrointestinal Tolerability of DMMET 01 (Glycinate of Metformin): Results of a Prospective Randomized Trial in Healthy Volunteers," Jun. 2009, Diabetes—Clinical Therapeutics/New Technology, vol. 58, No. Suppl. 1, pp. A533, Abstract No. 2074-PO, American Diabetes Association, United States (2009).

International Search Report and Written Opinion for International Application No. PCT/IB2008/002665, European Patent Office, Netherlands, mailed on Mar. 17, 2009, 7 pages.

* cited by examiner

*Primary Examiner* — Johnny F Railey
(74) *Attorney, Agent, or Firm* — Sterne, Kessler, Goldstein & Fox P.L.L.C.

(57) ABSTRACT

The present invention relates to metformin glycinate salt and pharmaceutical compositions thereof for the treatment of diabetes mellitus. The method includes administration of the metformin glycinate salt by various routes selected from oral, intravenous injectable, intramuscular injectable, nasal, intraperitoneal, or sublingual, in order to achieve a reduction in blood glucose levels. The invention further relates to the synthesis of a new 1,1-dimethylbiguanide glycinate salt, called Metformin Glycinate. The resulting salt exhibits advantages over other metformin salts. These advantages are due, in the first place, to the fact that the glycine counterion exhibits hypoglycemic effects by itself. Moreover, the salt exhibits more rapid absorption, reaching higher plasma concentrations than those produced with metformin hydrochloride.

49 Claims, 11 Drawing Sheets

FIGURE 10

Kinetic of blood glucose [mg / dL]. Males. (N, Mean ± SD)

| Group | Item | Dose [mg / kg] | Blood collection at the time points [min] after oral administration | | | | | |
|---|---|---|---|---|---|---|---|---|
| | | | 5 | 10 | 15 | 30 | 60 | 180 |
| A | Vehicle | - | 10 | 10 | 10 | 10 | 10 | 10 |
| | | | 124.9 ± 18.2 | 130.4 ± 12.7 | 152.4 ± 20.7 | 133.6 ± 14.2 | 122.6 ± 16.0 | 112.7 ± 21.4 |
| B | Metformin glycinate | 1500 | 10 | 10 | 10 | 10 | 10 | 10 |
| | | | 121.5 ± 15.2 | 137.5 ± 23.9 | 134.0 ± 29.7 | 128.2 ± 20.9 | 112.3 ± 15.5 | 77.3*** ± 29.9 |
| C | Metformin HCl | 1500 | 10 | 10 | 10 | 10 | 10 | 10 |
| | | | 119.9 ± 19.7 | 137.2 ± 16.5 | 138.5 ± 21.9 | 130.1 ± 20.4 | 103.2* ± 12.8 | 91.3 ± 22.3 |
| D | Glycine | 871.6 | 10 | 10 | 10 | 10 | 10 | 10 |
| | | | 111.5 ± 14.5 | 120.6 ± 12.2 | 128.2 ± 12.9 | 126.2 ± 14.4 | 117.1 ± 11.1 | 99.4 ± 10.4 |

FIGURE 11

Table 4: Kinetic of blood glucose [mg / dL]. Females. (N, Mean ± SD)

| Group | Item | Dose [mg / kg] | Blood collection at the time points [min] after oral administration | | | | | |
|---|---|---|---|---|---|---|---|---|
| | | | 5 | 10 | 15 | 30 | 60 | 180 |
| A | Vehicle | | 10 | 10 | 10 | 10 | 10 | 10 |
| | | | 112.8 ± 17.3 | 134.9 ± 22.8 | 146.2 ± 19.9 | 141.6 ± 20.3 | 116.6 ± 15.0 | 114.1 ± 16.9 |
| B | Metformin glycinate | 1500 | 10 | 10 | 10 | 10 | 10 | 9 |
| | | | 111.1 ± 11.5 | 115.6 ± 12.4 | 113.6^/^ ± 19.1 | 110.8^ ± 27.1 | 113.6 ± 33.8 | 34.7***/^/^^ ± 21.0 |
| C | Metformin HCl | 1500 | 10 | 10 | 10 | 10 | 10 | 10 |
| | | | 111.6 ± 13.2 | 119.3 ± 15.3 | 120.4 ± 19.2 | 116 ± 16.4 | 102.5 ± 11.9 | 68.8*** ± 26.4 |
| D | Glycine | 871.6 | 10 | 10 | 10 | 10 | 10 | 10 |
| | | | 128.0 ± 23.0 | 134.9 ± 31.4 | 144.7 ± 33.9 | 118.2 ± 36.4 | 106.3 ± 26.0 | 105.9 ± 25.0 |

METFORMIN GLYCINATE FOR BLOOD GLUCOSE CONTROL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a continuation-in-part application of PCT/IB2008/002665 filed on Jun. 26, 2008, published under WO2009/144527 on Dec. 3, 2009, all of the disclosure of which is incorporated herein by reference.

TECHNICAL FIELD OF THE INVENTION

This invention relates to metformin glycinate salt, which exhibits superior hypoglycemic properties, greater bioavailability a particular, safe pharmacokinetics. The invention further relates to pharmaceutical compositions of metformin glycinate salt and the use of these compositions for the treatment of diabetes mellitus and other associated diseases.

TECHNICAL BACKGROUND

The class of anti-diabetic drugs called biguanides originates from the Galega officinalis plant, which has been known for several centuries for its capacity to reduce the symptoms of diabetes mellitus. Metformin is a compound derived from biguanides that primarily acts by reducing hepatic gluconeogenesis, but also reduces glucose absorption at the gastrointestinal tract level and increases sensitivity to insulin by increasing the peripheral utilisation of glucose. This may be due to the fact that metformin improves the binding of insulin to its cellular receptor, which is explained by the increased activity that it induces in the tyrosine kinase postreceptor and the consequent increase in the number and activity of GLUT4 carriers.

Metformin is not metabolized; it is directly excreted in the urine. Its half-life is 6.2 hours.

Metformin and metformin hydrochloride have poor intestinal absorption at the colon and the lower gastro-intestinal tract level.

This invention relates to the development of a new biguanide salt based on metformin conjugated with Glycine, which exhibits a better absorption and passage into the bloodstream, less gastro-intestinal adverse effects and a better pharmacokinetic profile as compared to other metformin salts known in the prior art.

One disadvantage of metformin hydrochloride is that it is hygroscopic. This hinders the industrial handling thereof to prepare solid compositions such as tablets, capsules, etc. Moreover, in its solid form, it is a corrosive crystal, which wears the tabletting machines used. Furthermore, it is an extremely bitter salt for users and the acid generated thereby often causes gastric disorders with prolonged use.

Patent GB 1473256 discloses, for the first time, biguanide salts for treating metabolic disorders, especially diabetes mellitus, by reducing blood glucose levels, with the following formula:

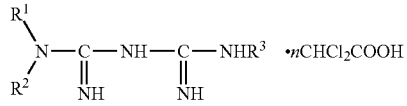

where $R^1$ represents a hydrogen atom or a lower alkyl or a lower alkenyl group and $R^2$ represents a lower alkyl, aryl, aryl-(lower alkyl), or an aryloxy-(lower alkyl) group or $R^1$ and $R^2$ together represent a lower alkenyl group, $R^3$ represents a hydrogen atom or a group with the formula:

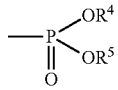

Where $R^4$ and $R^5$ each represent a hydrogen atom or a cation or $R^4$ represents a hydrogen and $R^5$ represents a lower alkyl group, or $R^4$ and $R^5$ together represent a lower alkylene group, and n means 1 or 2.

Unlike other biguanides, such as buformin or phenformin, metformin does not cause lactic acidosis at high serum levels. Metformin hydrochloride is the currently marketed salt and has the following formula:

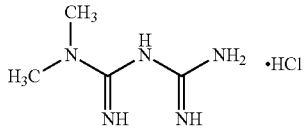

Metformin Hydrochloride

Belgian patent BE 568,513 discloses acid addition salts of metformin, including metformin hydrochloride. Patent application US 2005/0158374 discloses metformin associated with fatty acids, with improved adsorption at the gastrointestinal tract level. This metformin associated with a fatty acid (such as laureate, succinate, caprate, palmitate, etc.) is produced from a metformin salt (for example, metformin-HCl). These compounds were created in order to increase absorption at the lower gastro-intestinal tract level and for the drug to remain in the blood of patients who so require at relatively constant levels throughout the day, which avoids the intake of several daily doses. The plasma concentrations of these compounds measured in rats in ηg/ml with respect to time in hours show a greater bioavailability than metformin salts which are not bound to fatty acids. However, unlike metformin-fatty acid compounds, metformin glycinate not only reaches the maximum plasma level within the first few minutes, but these sane levels remain in plasma in a sustained manner for the first 3 to 4 hours, with a gradual decrease for 10 hours following intake. (FIG. 1)

This phenomenon exhibited by metformin glycinate is particularly advantageous to reduce glycemia, due to the high concentrations that it reaches in the first hour and which may be particularly useful in dealing with postprandial hyperglycemia, which has been recognized as one of the main factors for cardiovascular risk and vascular damage. On the other hand, since it reaches higher maximum concentrations than metformin hydrochloride, metformin glycinate requires lower doses to produce similar hypoglycaemic effects.

Another document that pertains to the state of the art is European patent EP 1039890 from Bristol-Myers Squibb Company, which addresses various dicarboxylic acid salts of metformin, in combination with another anti-diabetic agent, and a metformin fumarate, metformin succinate and metformin maleate. Similarly, there are other patents in the state of the art that relate to metformin salts, such as U.S. Pat. No. 4,835,184, which discloses the p-chlorophenoxyacetic salt of metformin, French patents FR 2320735 and FR 2037002, which disclose the pamoate salt of metformin, U.S. Pat. No. 3,957,853, which discloses the acetylsalicylate salt of metformin, German patents DE 2357864 and DE1967138, which disclose the nicotinic acid salt of metformin, Japanese patent JP 64008237, which discloses hydroxyacid salts of metformin, including salts of hydroxy-aliphatic dicarboxylic acids, such as mesotartaric acid, tartaric acid, mesoxalic acids and oxidised maleates; it may be observed that all these are organic acid salts of metformin.

In this invention, a new 1,1-dimethylbiguanide Glycinate salt was synthesized, called Metformin Glycinate. This salt exhibits advantages over other Metformin salts. These advantages are due, in the first place, to the fact that the glycine counterion exhibits hypoglycemic effects by itself. Moreover, this salt exhibits more rapid absorption, reaching higher plasma concentrations than those produced with metformin hydrochloride (FIG. 1). On the other hand, the glycine that is generated when the salt is ionized is not a strong acid; consequently, undesirable gastric effects are reduced. Finally, metformin glycinate has favorable physical characteristics for industrial-scale handling, thus facilitating the preparation of pharmaceutical compositions, since it is less corrosive, has better rheological properties and is less susceptible to compacting.

The synthesis was synthesized from the Metformin Hydrochloride salt, where free Metformin was produced by releasing the hydrochloride counterion, using an ion-exchange column for this purpose; the Metformin base released was dissolved in an aqueous medium and, subsequently, glycine was added at ambient temperature under constant stirring; subsequently, the resulting product is heated until a concentrated solution is produced, an organic solvent is added which does not react with the components present and wherein glycine is insoluble in order to create insolubility in the medium and favor crystallization of the saturated medium; all this in order to precipitate the excess glycine and then separate it by filtering; the filtrate was concentrated again until precipitation of the metformin glycinate salt was achieved.

Statistically significant differences (*) $P_{value}<0.05$, (**) $P_{value}<0.01$ compared to the control group by using the multiple Dunnett test.

Figure 9:
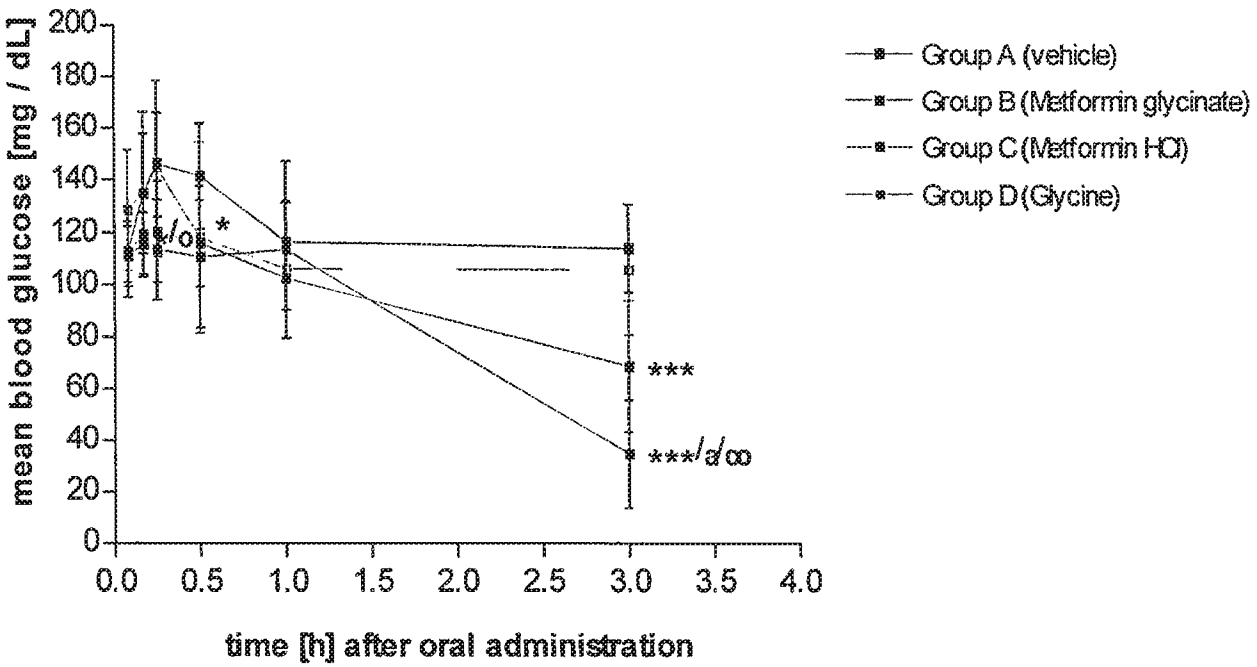

FIG. 9 Glucose kinetic curves. Females. (Mean±SD)

Statistically significant differences (*) $P_{value}<0.05$, (***) $P_{value}<0.001$ compared to the control group by using the multiple Dunnett test.

Statistically significant differences ($^a$) $P_{value}<0.05$, comparison between group B and C.

Statistically significant differences ($^{oo}$) $P_{value}<0.01$, comparison between group B and D.

FIG. 10 Kinetic of blood glucose [mg/dL]. Males. (N, Mean±SD) (*) $P_{value}<0.05$, (***) $P_{value}<0.001$, statistically significant differences compared the control group using the multiple Dunnett test were recorded.

FIG. 11 Kinetic of blood glucose [mg/dL]. Females. (N, Mean±SD)

(*) $P_{value}<0.05$, (**) $P_{value}<0.01$, statistically significant differences compared the control group using the multiple Dunnett test were recorded.

($^a$) $P_{value}<0.05$, statistically significant differences between group B and group C using the multiple Tukey test were recorded.

($^o$) $P_{value}<0.05$, ($^{oo}$) $P_{value}<0.01$ statistically significant differences between group B and group D using the multiple Tukey test were recorded.

DESCRIPTION OF THE INVENTION

Below, we specify a preferred embodiment, which is not intended to limit the synthesis of the metformin glycinate salt, which was synthesized from the metformin hydrochloride salt, where free metformin was produced by releasing the hydrochloride counterion, using an ion-exchange column for this purpose; the metformin base released was dissolved in an aqueous medium and, subsequently, glycine was added at ambient temperature under constant stirring; subsequently, the resulting product is heated until a concentrated solution is produced, an organic solvent is added which does not react with the components present and wherein glycine is insoluble in order to create insolubility in the medium and favor crystallization of the saturated medium; all of this in order to precipitate the excess glycine and then separate it by filtering; the filtrate was concentrated again until precipitation of the metformin glycinate salt was achieved, this precipitate is washed and purified.

The salt produced was identified by means of nuclear magnetic resonance, infrared spectrometry, mass spectrometry and, finally, Monocrystal X-ray Diffraction. The analysis of the spectra indicated that the new salt produced is different from other metformin compounds.

The Nuclear Magnetic Resonance (NMR) proton spectrum showed displacements at 2,814 ppm, 2,916 ppm, and 4,677 ppm.

The 13C spectrum showed at 37,754 ppm, 44,824 ppm, 158,761 ppm, 160,308 ppm, and 180,049 ppm.

The infrared spectrum (IR) showed characteristic absorption signals at 3,367.34 $cm^{-1}$, 3,175.88 $cm^{-1}$, 1,618.78 $cm^{-1}$, and 1,573.96 $cm^{-1}$.

The mass spectrum was obtained by the $FAB^+$ technique, and a molecular ion was obtained al 259 m/z, which is consistent with the expected compound, where will be remember that the molecular ion is equal to molecular weight by two plus one, this is: 129×2+1=259

The other mass spectrum was obtained by the FAB⁻ technique, and a molecular ion was obtained at 75 m/z which is consistent with the expected compound The monoocrystal X-ray diffraction obtained corresponds to a triclinic crystal, of spatial group P-1, with the following unit cell dimensions:

a=5.993 A°
b=8.673 A°
c=10.51 A°
$\alpha$=90.94°
$\beta$=95.10°
$\gamma$=107.58°

Characteristics of Metformin Glycinate:

a) Full chemical name:
N,N-dimethylimidodicarbonimidic diamide glycinate.

b) Condensed formula:

$C_6H_{16}N_6O_2(C_4H_{11}N_5 \cdot C_2H_5NO_2)$

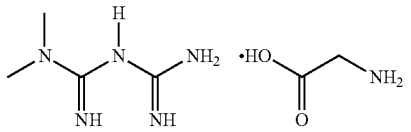

c) Molecular weight:
204.24 d) Storage requirements:
Keep in well-closed containers at ambient temperature.

e) Solubility data
Highly soluble in water, freely soluble in methanol, ethanol. Insoluble in ethyl acetate, ether, chloroform, benzene. Solubility in water approximately 1.4 g/ml at 25° C.
Melting point: 166° C.-172° C.

f) State: Solid (powder)

g) Chemical stability: by reaction with a strong acid, metformin glycinate produces a new metformin salt, and a new glycine salt is produced by reaction of he basic part of glycine.

Administration of the compound of the present invention, in pure form or in an appropriate pharmaceutical composition, can be carried out via any of the accepted modes of administration of agents for serving similar utilities. The pharmaceutical compositions of the invention can be prepared by combining a salt of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage unit, where for example, a tablet may be a single dosage unit, and a container of a salt of the invention in aerosol form may hold a plurality of dosage unit. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or pharmaceutically compositions thereof, for treatment of a disease-state associated with the hypoglycemic activity in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present salts, one or more of a sweetening agent, preservatives, dye/colorant and flavor enhancer. In a composition intended to be administered by injection, one or more of a surfactant, preservative, wetting agent, dispersing agent, suspending agent buffer, stabilizer and isotonic agent may be included.

The liquid pharmaceutical compositions of the invention, whether they be solutions, suspensions or other like form, may include one or more of the following adjuvants:

sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a salt of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredient. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutical compositions, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drag combination; the severity of the particular disorder or condition; and the subject undergoing therapy. Generally, a therapeutically effective daily dose is from about 0.1 mg to about 20 mg/kg of body weight per day of a compound of the invention or a pharmaceutically compositions thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of the therapeutic agents described above in the Utility of the Compounds of the Invention. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the patient together in a single oral dosage composition such as a tablet or capsule, or each agent administered in separate oral dosage formulations. Where separate dosage formulations are used, the compounds of the invention and one or snore additional active agents can be administered at essentially the same time, i.e., concurrently, or at separately staggered times, i.e., sequentially; combination therapy is understood to include all these regimens.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing the active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient preferably 0.1-85%, typically 75-95%.

The active compounds or pharmaceutically acceptable derivatives may be prepared with carriers that protect the compound against rapid elimination from the body, such as time release formulations or coatings. The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with hypoglycemic activity is implicated. It is to be understood that such combination therapy constitutes a further aspect of the compositions and methods of treatment provided herein.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, marmitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agent include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions amid/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene laurel ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. in addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleafie and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous ornonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN.RTM. 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically, a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials or lyophilization. Each vial will contain a single dosage (10-1000 mg, preferably 100-500 mg) or multiple dosages of the compound. The lyophilized powder can be stored under appropriate conditions, such as at about 4.degree. C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per ml of sterile water or other suitable carrier. The precise amount depends upon the selected compound. Such amount can be empirically determined.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In the above-described methods, the metformin glycinate salt may be administered either alone or in combination with one or more additional active agents. Combination therapy includes administration of a single pharmaceutical dosage formulation which contains metformin glycinate salt and one or more additional active agents, as well as administration of metformin glycinate salt and each active agent in its own separate pharmaceutical dosage formulation. For example, metformin glycinate salt and an HMG-CoA reductase inhibitor can be administered to the patient together in a single oral dosage composition such as a tablet or capsule, or each agent administered in separate oral dosage formulations. Where separate dosage formulations are used, the metformin glycinate salt and one or more additional active agents can be administered at essentially the same time, i.e., concurrently, or at separately staggered times, i.e., sequentially; combination therapy is understood to include all these regimens.

For example, the metformin glycinate salt may be administered in combination with one or more of the following active agent: an antihyperlipidemic agent a plasma HDL-raising agent an antihypercholesterolemic agent, such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor, such as melinamide; probucol; nicotinic acid and the salts thereof and niacinamide; a cholesterol absorption inhibitor such as beta-sitosterol; a bile acid sequestrant anion exchange resin, such as cholestyramine, colestipol or a dialkylaminoalkyl derivatives of a cross-linked dextrin; an LDL (low density lipoprotein) receptor inducer; fibrates such as clofibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); anti-oxidant vitamins, such as vitamin C and E, and beta carotene: a betablocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the metformin glycinate salt can be administered in combination with more than one additional active agent, for example, a combination of metformin glycinate salt with an HMG-CoA reductase inhibitor and aspirin, or metformin glycinate salt, with an HMG-CoA reductase inhibitor and a beta blocker. Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927) 5: 1061-1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105-11 (1974); and Laakso, M. and Lehto, S., Diabetes Reviews (1997) 5(4): 294315). Several lipoprotein abnormalities have been described among diabetic subjects (Howard B., et al., Arteriosclerosis (1978) 30: 153-162).

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., J. Basic & Clin. Phys. & Pharm. (1998) 9: 387-406 and Flier, J. Ann Rev. Med. (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plasminogen activator inhibitor-1), has been referred to as "Syndrome X" (see, e.g., Reaven, G. M., Physiol. Rev. (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Type 2 diabetes often occurs in the face of normal, or even elevated, levels of insulin and can result from the inability of tissues to respond appropriately to insulin. Most type 2 diabetic patients are insulin resistant and have a relative deficiency of insulin, in that insulin secretion can not compensate for the resistance of peripheral tissues to respond to insulin. In addition, many type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of type 1 or type 2 diabetes.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "treating" means the management and care of a human subject for the purpose a combating the disease, condition, or disorder and includes the administration of a compound of the present invention to prevent the onset of the symptoms or complications, alleviating the symptoms or complications, or eliminating the disease, condition, or disorder.

As used herein and in the claims, "treating hyperglycemia " refers to slowing, interrupting, arresting, or stopping the failure to maintain appropriate blood sugar levels in the body, and does not necessarily indicate total elimination of metabolic defects in production and utilization of glucose.

By the term "effective amount" what is meant is an amount which is effective for either prophylactic or therapeutic purposes to prevent or mitigate the failure to maintain appropriate blood sugar levels n the body or reduce blood glucose level in question.

Metformin glycinate is a biguanide with pharmacological properties different from that of metformin chlorydrate (generic drug). The metformin glycinate acts by inhibiting the liberation of hepatic glucose and increasing the peripheral sensitivity to endogenous insulin to promote attachment of insulin in the receptor. This is why we take into consideration an antihyperglycemic agent in as much as the manner prevents the increase in the quantity of glucose. However, the differences between metformin chlorhydrate, metformin glycinate have been demonstrated in the possession of hypoglycemic effect in preclinical and clinical research, by the decreasing amount of plasma glucose in a direct manner. Although the mechanism of action for which the cause and effect has not yet been defined, it has been seen to be consistent in various studies. In one study, it has been observed that the glycemic curve after acute oral administration of metformin glycinate in rats has pronounced effect on hypoglycemic rats when the medicament was administered, as compared to rats where metformin chlorhydrate was administered. In another study, the toxicity evaluation of metformin glycinate was determined where it was orally administered repeatedly in rats during 28 days, a different dosage as compared with metformin chlorhydrate. With the obtained results, it was concluded that there were no differences in so far as toxicity profile between metformin glycinate and metformin chlorhydrate at high dosage. Although the observed differences in relation to the clinical pathological results demonstrate a severe hypoglycemia suggesting pharmacological effect was exaggerated (excessive) and indicated a pharmacological activity much distinct between the two drugs.

The solid pharmaceutical composition contains pharmaceutical excipients of about 10-50% of one or more combination of microcrystalline cellulose, lactose, dibasic calcium phosphate, dextrose, calcium carbonate, magnesium carbonate, maltodextrin, mannitol, compressed sugar, sorbitol, etc.; disintegrants include about 1-15% of one or more combination of sodium crosscarmellose, crospovidone, starch, pregelatinized starch, etc.

Binders include about 1-15% of one or more of combination of povidone, dextrin, maltodextrin, polymethacrylates, alginate, sodium alginate, carboxymethylcellulose, ethylcellulose, starch, pregelatinized starch, gelatin, gum tragacanth, etc. Glidants include about 0.1-15% of one or more combination of talc, colloidal silicon dioxide, magnesium trisilicate, starch etc.; lubricant is about 0.5-7% of one or more combination of magnesium stearate, zinc stearate, calcium stearate, glycerol monostearite, glycerylpalmitylstearate, polyethyleneglycol, sodium benzoate, sodiumlaurylsulfate, sodium stearyl fumarate, stearic acid, etc.; polymers include about 0.3-5% of one or more combination of methylcellulose, hydroxypropylcellulose, hydroxypropylmethylcellulose, ethylcellulose, polymethacrylates, polyvinylalcohol, etc.

Solid pharmaceutical composition preferably contains about 20% anhydrous dibasic calcium phosphate, about 5% povidone, about 5% starch sodium glycolate, about 0.3% colloidal silicon dioxide, about 5% talc, about 1% magnesium stearate, and about 0.7% coating.

The recommended dosage is at least about 1050.6 mg once or twice a day. The dosage range is about 100 mg to about 3.5 g. The dosage of metformin glycinate is adjusted gradually in response to how well it is tolerated and how well the patients blood sugar levels respond to the drug.

The studies specified below are a preferred embodiment of the invention, but are not intended to limit either the compositions to be administered, which may be in the form of a tablet, caplet, gel, paste, powder, prolonged-release granules, capsule, prolonged-release tablet, liquid with buffer agent, effervescent tablets, suspension, syrup, aerosol and others, or the administration route, which may be oral, intravenous injectable, intramuscular injectable, nasal, intraperitoneal, sublingual, etc.

In vitro Cytotoxicity Study of Metformin Glycinate.

The following primary cell lines and cell cultures were used:

Hepatic origin cells: CCL13, ATCC (American Type Culture Collection).

Kidney origin cells: CRL 1633, ATCC (American Type Culture Collection).

Primary cultures: hepatocytes.

The following cytotoxicity parameters were evaluated:

Cell morphology and cell adhesion.

Methylthiazoltetrazolium reduction assay (MTT Assay).

The concentration range evaluated was from 250 mg/ml to 0.12 mg/ml.

Two exposure times were evaluated: 24 and 72 hours.

Results:

The metformin glycinate evaluated was not cytotoxic for any of the cell types used in this study in the two exposure periods evaluated (24 and 72 hours).

Median Lethal Dose Study ($LD_{50}$) for Metformin Glycinate.

The oral-route 50 Lethal Dose ($LD_{50}$) assay in Wistar rats was performed in compliance with international regulations and the specifications for the care and use of laboratory animals. The entire procedure was conceived as stipulated in Guideline 423 of the Guidelines of the Organization for Economic Co-operation and Development.

Number of animals: 96 Wistar rats, young adults 3 months of age, of both sexes, were used.

Randomization: 12 batches with 8 animals per batch. Four batches were used for the preliminary studies to find the dose interval and eight batches were used for the final study.

Method: After fasting, different doses of the product were orally administered using an orogastric tube. During the development of the study, a control group was used in parallel.

Volume: 3.8±0.4 ml (corresponding to a volume not greater than 2 ml for every 100 g of rat body weight).

Observation period: 24 hours.

Results:

The oral $LD_{50}$ obtained for Metformin glycinate: 2.4625±0.195 g/kg. (The $LD_{50}$ of Metformin hydrochloride is 1.45 g/kg.)

The $X^2$ test had a value of p=0.723.

The OECD defines $LD_{50}$ as the "statistically derived single dose of a substance that can be expected to cause death in 50% of the laboratory animals."

Subacute Toxicity Study for Metformin Glycinate.

The Subacute Toxicity test at 28 days was performed in compliance with international regulations and the specifications for the care and use of laboratory animals.

Number of animals: 50 Wistar rats, young adults 3 months of age, of both sexes, were used. Five batches with ten animals each. Four experimental groups (10 animals in each group) and a control group.

After fasting, different doses (low, medium, high, and satellite and control groups) of the product were orally administered using an orogastric tube.

Doses Used:

Low: 0.1 g/kg

Medium: 0.5 g/kg

High: 1.0 g/kg

Satellite 1.0 g/kg

Control: Only the carrier (Bidistilled water)

Observation Period: 28 days. Satellite Group 15 days post-treatment (28+15). During the 28 days, the following studies were performed: Observation of the appearance of signs and symptoms, haematological tests and anatomic-pathological study. The entire procedure was conceived as stipulated in Guideline 407 of the Guidelines of the Organization for Economic Cooperation and Development.

Results:

Clinical observations: Semi-pasty feces at high doses (duration 2 days). No mortality was observed during the 28-day study. No behavioral changes were observed. The autopsies did not show drastic changes in the different organs.

Anatomic-pathological study: No significant macroscopic changes were observed in the target organs.

Control Group: No alterations were observed.

Post-Study Observations:

Since there was no documentation prior to performing this study, one may conclude that the presence of semi-pasty faeces at the high dose and in the satellite group is a potential adverse effect only at the high dose administered.

The possibility of determining any long-term adverse effects (after 28 days) was not demonstrated, since no subsequent effects were demonstrated following the last administration of the drug.

The probable adverse effects observed with the high dose (semi-pasty faeces) were reversed during the course of the study (9th-11th day).

The extrapolation of a probable dose to determine the non-observable adverse effect could be set between 0.5 and 1.0 g/kg.

Figure 1:
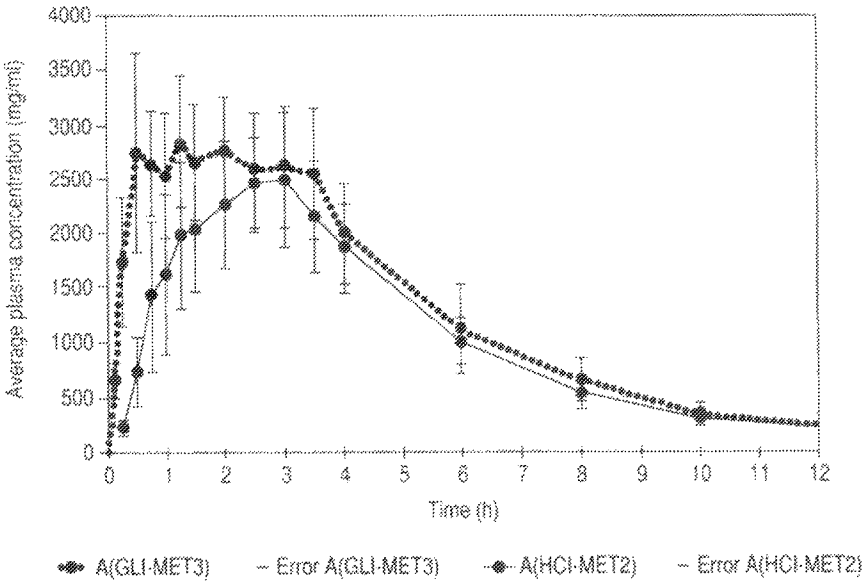
FIG. 1, shows the plasmatic concentration of Metformin glycinate (GLI-MET3), compared with Metformin clorhidrated (HCL-MET2)
Figure 2:
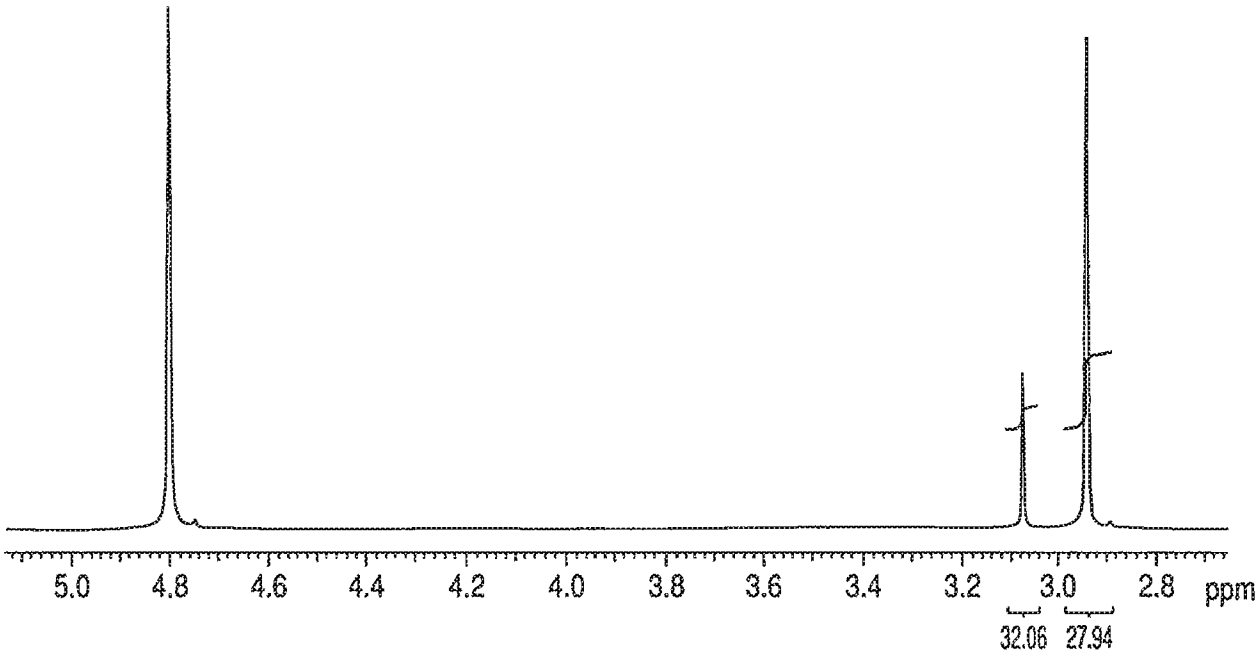
FIG. 2, shows Proton Nuclear Magnetic Resonance spectra (NMR) for Metformin glycinate.
Figure 3:
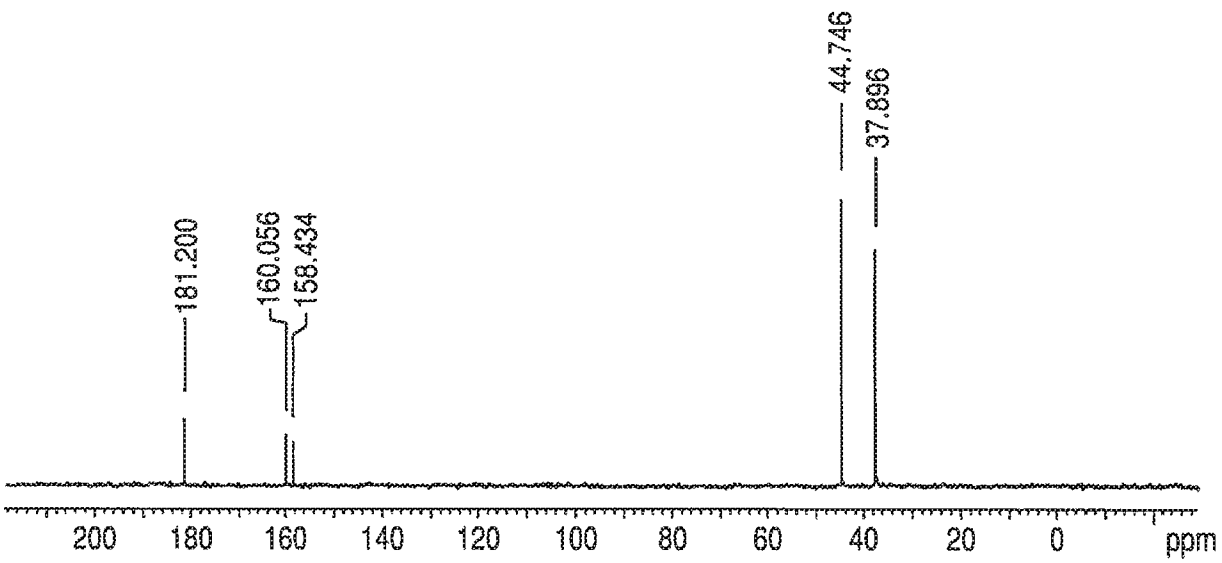
FIG. 3, shows Carbon-13 (NMR) spectra for Metformin glycinate.
Figure 4:
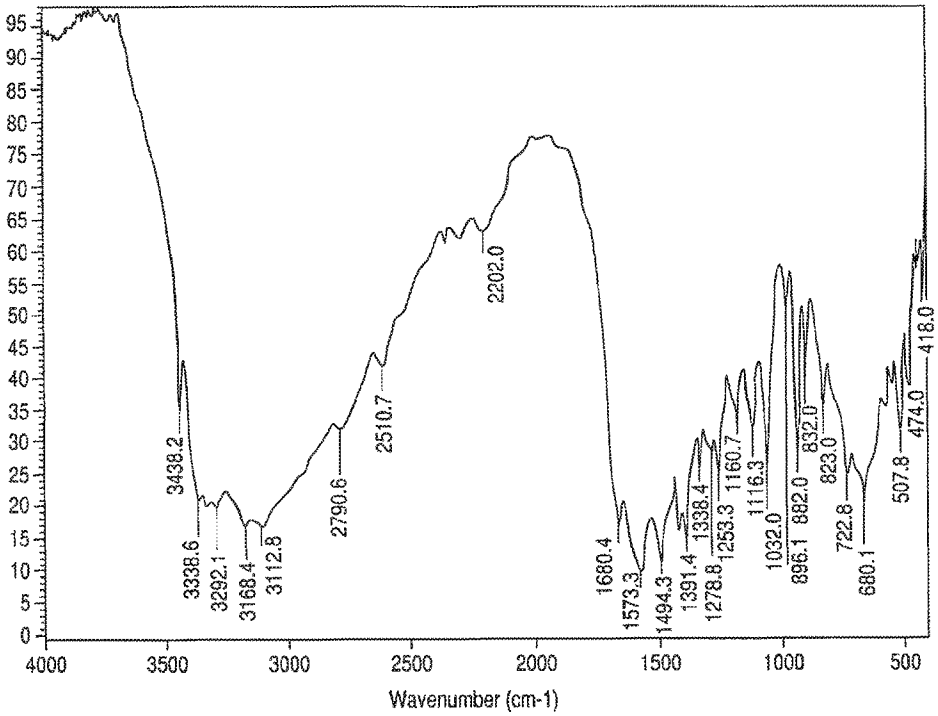
FIG. 4, shows Infra-red (IR) spectra for Metformin glycinate.
Figure 5:
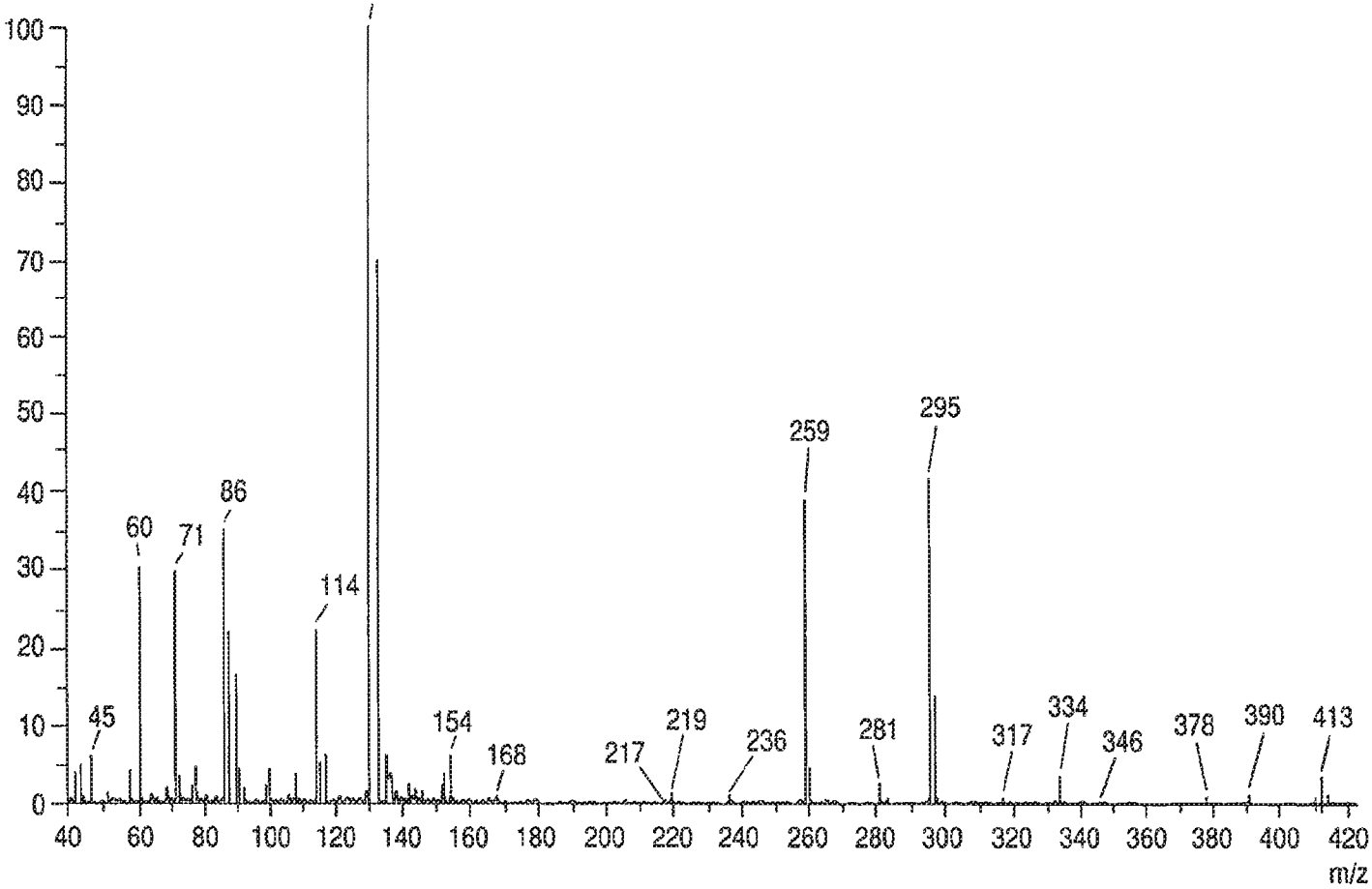
FIG. 5, shows mass spectra for metformin glycinate obtained for $FAB^+$ technique where molecular ion of cation is in 259 m/z and $FAB^-$ where molecular ion is in 75 m/z.
Figure 6:
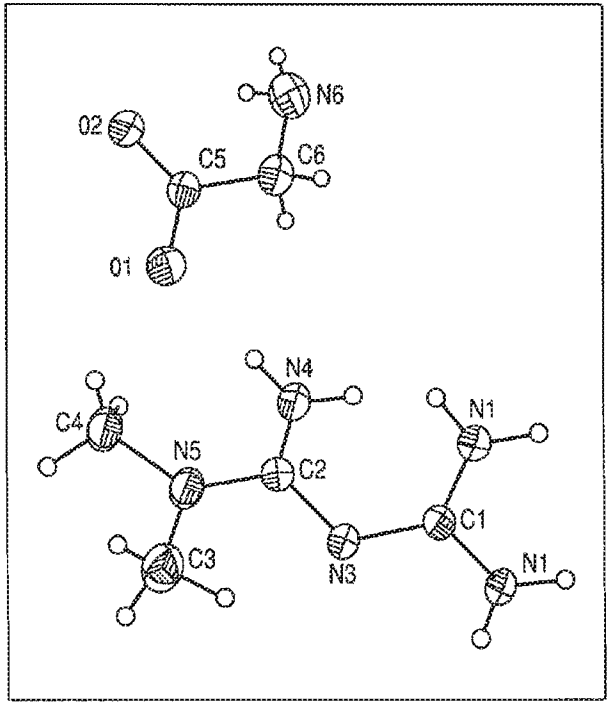
FIG. 6, shows unitary cell obtained for X ray diffraction of monocrystal.
Figure 7:
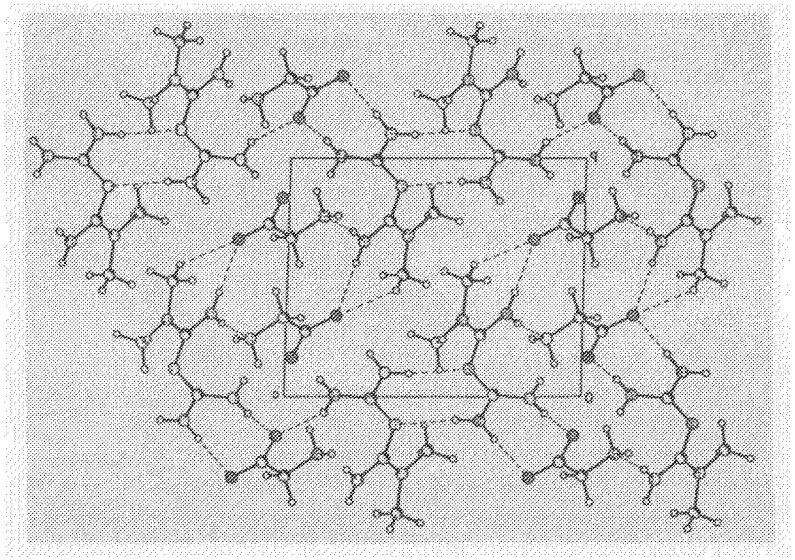
FIG. 7, shows crystalline array obtained from X ray diffraction.
Figure 8:
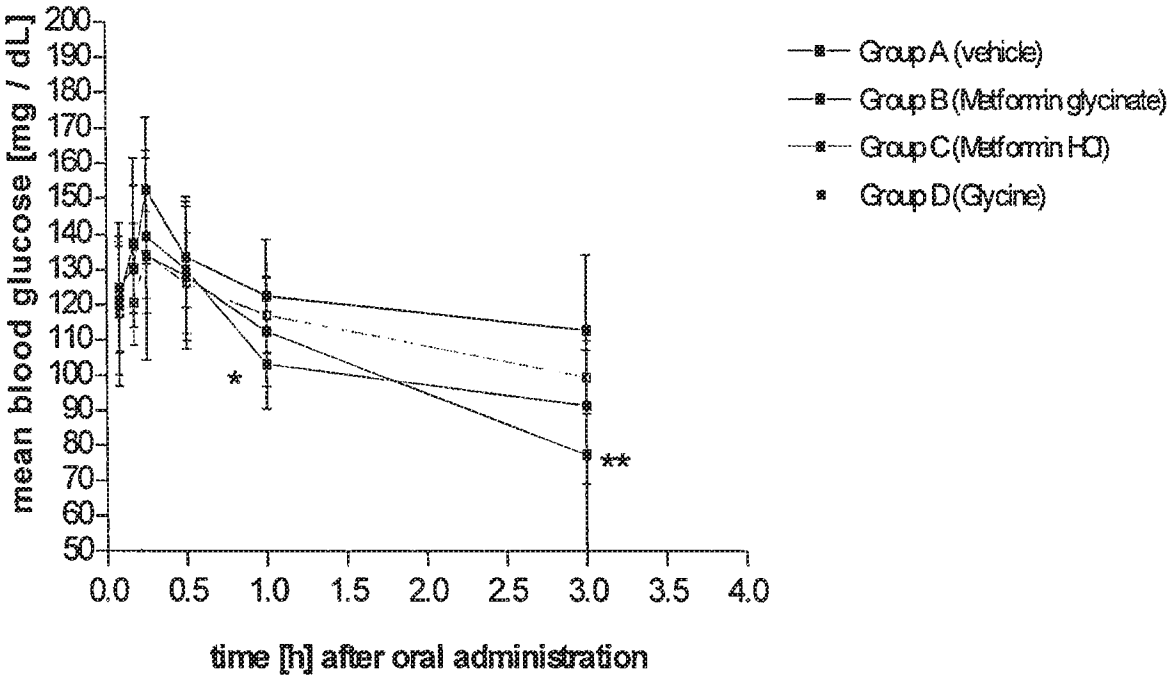
FIG. 8 Glucose kinetic curves. Males. (Mean±SD)

Bioavailability Study for Metformin Glycinate metformin glycinate tablets equivalent to 850 mg of metformin hydrochloride (HCl-Metformin) were administered to 12 healthy volunteers and were compared to the response of 12 other volunteers who received metformin hydrochloride 850 mg. Samples were taken from the 24 volunteers in order to perform a pharmacokinetic curve, with the following resulting pharmacokinetic parameters: maximum concentration ($C_{max}$) 591 ng/ml, maximum time ($t_{max}$) 2.5 hours, area under the curve for 10 minutes at 24 hours ($ABC_{(10-24)}$) 26.811 ηg·ml/h, with a relative bioavailability of 2.8 μg/ml (see results in FIG. 1).

Metformin glycinate begins its biodegradation and its release during the first few minutes; consequently, there is rapid absorption, with the appearance of plasma levels between 0.00 and 0.13 h. These levels remain in circulation for over 10.00 hours.

The circulating remnant (levels below 200 ηg/ml) is present and tends to decrease within the next 12 hours and disappears when the drug is not administered, the following morning.

Study of Gastric Tolerability and Adverse Events for Metformin Glycinate.

A study was performed in 24 healthy volunteers who were administered one tablet of Metformin glycinate (12 volunteers) or Metformin hydrochloride (12 volunteers) in a dose equivalent to 850 mg for 30 days, continuously at the same time. An endoscopy was performed prior to the first drug intake and another was performed at the end of the 30-day study.

In this study, the Lanza Score, which is used to evaluate gastric damage by measuring the sum of ranges, was used. The higher the mean range, the greater the gastric damage.

In this study, we found that the group that received Metformin glycinate had a mean range sum of 225 versus 258 for the group that received Metformin hydrochloride (p=0.43).

Although statistically significant differences are not observed, we did find that the group that received metformin glycinate suffered less gastric damage than the group that received metformin hydrochloride, who had a greater proportion of volunteers with a Lanza Score of 4 (maximum score in the scale).

In the patient follow-up, in search of serious adverse events, neither of the two groups showed any, which corroborates the safety of both drugs.

Blood Glucose Determination

The present acute toxicity study showed that one single oral administration of metformin glycinate at a dose of 1500 mg/kg, or Glycine at a dose of 871.6 mg/kg, (equivalent to glycine content in the proven dose of metformin glycinate), administered in two groups of 10 Sprague Dawley rats 10 males and 10 females (20 rats per groupe), and one group of 20 rats received only the vehicle, as control group. The following 14 days to administration, toxic effects were evaluated. Following different times after the administration, glucose levels were determined (5, 10, 15, 30, 60, 180 and 360 minutes); (the administered metformin basal dose was selected near to lethal dosage); six hours after administration complete blood biochemistry was analyzed, obtaining a mortality of 30% in females versus 10% in females administered orally with metformin HCl at the same dose In males, either the test item Metformin glycinate or the reference items Metformin HCl and Glycine did not show mortality. The cause to deaths was to a pronounced and fast drop in glycemia levels.

The study showed that the pharmacological effect of metformin glycinate, reflected in reduction of blood glucose and increase of lactate level in plasma on the day of oral administration, is more pronounced in females than in males and also more pronounced than in animals treated with metformin glycinate. Both effects are well known from metformin HCl and are signs for an increased cellular glucose uptake and stimulation of anaerobic glycolysis. Glycine, used at the equimolar dose of glycinate (871.6 mg/Kg), did not show a marked glucose reducing affect. This result suggests that the more pronounced reduction of glucose levels in the group receiving metformin glycinate with respect to metformin HCl was not caused by a simple additive pharmacological effect of Glycine. FIGS. 8 to 11.

Emphasizing, it was observed that test item-related effect on blood glucose level after one single oral administration in males and more pronounced in females when compared to animals from the control group and also when compared to animals from the reference items groups. Females showed a statistically significant lower blood glucose level 15 min, 30 min and also 3 and 6 hours after a single oral administration with metformin glycinate when compared to females from the control group. Females treated with metformin HCl showed statistically lower blood glucose level 3 and 6 hours after oral administration when compared with females from the control group.

In general, the lowest level of glucose in blood was detected three hours after the oral single administration with metformin glycinate and metformin HCl in both sexes. The metformin glycinate described and claimed as the invention, show pharmacologic and pharmacokinetic properties different from metformin HCL properties, such differences makes them not bioequivalent salts making necessary to obtain pharmacokinetic activity and pharmacologic and security profiles. This new salt of Metformin has demonstrated to possess a different pharmacologic hypoglycemiant activity than clorhydrate salt of metformin, manifested in preclinical and clinical results, including human.

Due to all that disclosed above, any person skilled in the art may observe the novelty and inventive scope of the development of this new pharmaceutical salt for the treatment of diabetes; it is worth noting that the behavior of the drug plasma concentration curves shows a greater bioavailability not only as compared to metformin hydrochloride, but also to metformin salts with fatty acids; this is evident upon analyzing the differentials between the areas under the curves (see result FIG. 1); the high-concentration maintenance periods (four hours) have not been reported in the state of the art studied; this phenomenon is, therefore, an unexpected, advantageous result for the treatment of diabetic patients.

All publications and patent applications cited in this specification are herein incorporated by reference as if each individual publication or patent application were specifically indicated to be incorporated by reference. This invention has been described hereinabove, although with reference to a plurality of illustrative exemplary and preferred embodiments, it is to be understood that is in no way to be construed as limiting. However, it is readily appreciated that, from reading this disclosure, the invention may be embodied in other specific forms without departing from the spirit or essential characteristics or attributes to bring modifications by replacing some elements of this invention as practiced by their equivalents, which would achieve the same goal thereof and accordingly reference should be made to the appended claims, rather than to the foregoing specification, as indicating the scope of the invention. Accordingly, those skilled in the art will recognize, or be able to ascertain using no more than routine experimentation, many equivalents to the specific embodiments and the scope of the invention being indicated by the appended claims described herein. Such equivalents, obvious variations, and all changes which come within the meaning and equivalency of the claims are therefore intended to be encompassed therein and are deemed covered by the claims of this invention.

The invention claimed is:

1. [A salt which comprises metformin and glycinate, forming a metformin] *Metformin* glycinate salt, (N,N-dimethylimidodicarbonimidic diamide glycinate) having the formula as follows:

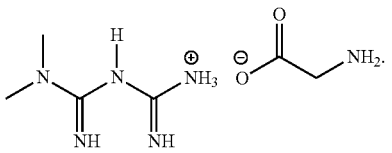

2. The metformin glycinate [salt] of claim 1, having a nuclear magnetic resonance (NMR) proton spectrum displacement at 2,814 ppm, 2,916 ppm, and 4,677 ppm.

3. The metformin glycinate [salt] of claim 1, having carbon-13 spectrum displacements at 37,754 ppm, 44,824 ppm, 158,761 ppm, 160,308 ppm, and 180,049 ppm.

4. The metformin glycinate [salt] of claim 1, having infrared (IR) spectrum characteristic absorption signals at 3,367.34 $cm^{-1}$, 3,175,88 $cm^{-1}$, 1,618.78 $cm^{-1}$, and 1,573.96 $cm^{-1}$.

5. The metformin glycinate [salt] of claim 1, wherein the monocrystal X-ray diffraction obtained corresponds to a triclinic crystal of spatial group P-1, with the following cell dimensions, a=5.993 A°
b=8.673 A°
c=10.51 A°
$\alpha$=90.94°
$\beta$=95.10°
$\gamma$=107.58°.

6. A pharmaceutical composition comprising an effective amount of *said* metformin glycinate [salt] of claim 1, as an active ingredient, said composition in the form of a tablet, caplet, gel, paste, powder, prolonged-release granules, capsule, prolonged-release tablet, liquid with buffer agent, effervescent tablets, suspension, syrup, aerosol or other pharmaceutical formulations.

7. The pharmaceutical composition of claim 6 comprising an effective amount of *said* metformin glycinate [salt] together with pharmaceutically acceptable diluent or carrier.

8. A tablet [formulation] comprising an effective amount of *said* metformin glycinate [salt as claimed in] *of* claim 1, or pharmaceutical composition thereof in admixture with excipients.

9. [A] *The* tablet [formulation as claimed in] *of* claim 8 wherein the excipients comprise a compression [an] additive to provide sheen to tablet, a disintegrant and a lubricant.

10. [A] *The* tablet [formulation as claimed in] *of* claim 8 wherein the excipients comprise microcrystalline cellulose, anhydrous dibasic calcium phosphate, sodium starch glycollate and magnesium stearate.

11. A capsule [formulation] comprising an effective amount of *said* metformin glycinate [salt as claimed in] *of* claim 1, or pharmaceutical composition thereof in admixture with excipients.

12. A method of producing [the] metformin glycinate [salt], comprising the following steps:

a) preparing [the] *a* solution of metformin hydrochloride;
b) separating the hydrochloride counterion by passing [a] *the* solution of metformin hydrochloride [salt] through ion-exchange column in order to produce free metformin;
c) dissolving the free metformin in an aqueous medium;
d) adding glycine to the aqueous medium at ambient temperature under constant stirring to obtain [the] *a* resulting mixture of glycine and metformin;
e) concentrating the resulting mixture;
f) adding a solvent wherein glycine is insoluble [is added] until [the] excess thereof precipitates;
g) filtering the mixture in order to eliminate the excess glycine;
h) evaporating the resulting filtrate until a second precipitate is produced; and
i) washing and purifying the second precipitate to obtain metformin glycinate [salt].

13. The method of claim 12, further comprising adding an organic solvent in (f) which does not react with the components present and wherein glycine is insoluble its order to create insolubility in the medium and favor crystallization of a saturated medium, and precipitate the excess glycine.

14. A method of treating hyperglycemia in warm-blooded animals, comprising administering a therapeutically effective amount of *said* metformin glycinate [salt as claimed in] *of* claim 1, or pharmaceutical compositions thereof.

15. The method of claim 14 comprising administering various doses of *said* metformin glycinate in an amount sufficient to achieve a reduction in blood glucose levels by various routes selected from oral, intravenous injectable, intramuscular injectable, nasal, intraperitoneal, or sublingual.

16. The method of claim 14 wherein said metformin glycinate [salt] exhibits about 40 fold reduction in glucose level as compared to metformin hydrochloride.

17. The method of claim 14 wherein said metformin glycinate [salt] or pharmaceutical compositions thereof modulates diabetes or treats diabetes and its related symptoms, complications and disorders.

18. The method of claim 14 wherein said metformin glycinate [salt] or pharmaceutical compositions thereof are administered at a dosage range of about 100 mg to about 3.5 g.

19. The metformin glycinate [salt] prepared from the method of claim 12.

20. The pharmaceutical composition of claim 6 wherein the metformin glycinate [salt] is in combination with one or more additional active agents.

*21. The metformin glycinate of claim 1, wherein said metformin glycinate melts at 166-172° C.*

*22. The metformin glycinate of claim 21, wherein said metformin glycinate has characteristic IR peaks of about 3,367 $cm^{-1}$, 3,175 $cm^{-1}$, 1,618 $cm^{-1}$, 1,573 $cm^{-1}$, and 1494 $cm^{-1}$.*

*23. A pharmaceutical composition comprising said metformin glycinate of claim 21 and one or more pharmaceutically acceptable excipients.*

*24. The pharmaceutical composition of claim 23, wherein said composition is a tablet or a capsule.*

*25. The pharmaceutical composition of claim 23, wherein said composition comprises about 1050 mg of said metformin glycinate.*

*26. The pharmaceutical composition of claim 23, wherein said one or more pharmaceutically acceptable excipients comprise dibasic calcium phosphate, povidone, starch sodium glycolate, colloidal silicon dioxide, talc, and magnesium stearate.*

*27. The pharmaceutical composition of claim 26, wherein said composition further comprises a coating.*

*28. The pharmaceutical composition of claim 27, wherein said composition comprises about 1050 mg metformin glycinate.*

*29. The pharmaceutical composition of claim 27, wherein said coating is an enteric coating.*

*30. The pharmaceutical composition of claim 29, wherein said metformin glycinate has characteristic IR peaks of about 3367 $cm^{-1}$, 1573 $cm^{-1}$, and 1494 $cm^{-1}$.*

*31. The pharmaceutical composition of claim 27, wherein the composition is a tablet.*

*32. The pharmaceutical composition of claim 20, wherein said one or more additional active agents comprise an antihyperlipidemic agent, a plasma HDL-raising agent, an antihypercholesterolemic agent, or a combination thereof.*

*33. The pharmaceutical composition of claim 20, wherein said one or more additional active agents are an HMG-CoA reductase inhibitor and aspirin.*

*34. The pharmaceutical composition of claim 20, wherein said one or more additional active agents are an HMG-CoA reductase inhibitor and a beta blocker.*

*35. A method of treating type 2 diabetes in a warm-blood animal comprising administering to said warm-blooded*

*animal in need thereof a therapeutically effective amount of said metformin glycinate of claim 21.*

*36. The method of claim 14, wherein said metformin glycinate is administered at a dose of about 1050 mg or said pharmaceutical composition comprises about 1050 mg metformin glycinate.*

*37. The method of claim 36, wherein said warm-blood animal is a human.*

*38. The method of claim 37, wherein said administration provides a $C_{max}$ of about 591 ng/ml, a $T_{max}$ of about 2.5 hours, and an $AUC_{(10-24)}$ of about 26 ng•ml/h.*

*39. The method of claim 37, wherein said human has type 2 diabetes.*

*40. The method of claim 37, wherein said administration is once a day or twice a day.*

*41. The method of claim 40, wherein said administration is once a day.*

*42. The method of claim 14, wherein said method further comprises administering one or more additional active agents to said warm-blooded animal.*

*43. The method of claim 42, wherein said one or more additional active agents comprise an antihyperlipidemic agent, a plasma HDL-raising agent, an antihypercholesterolemic agent, or a combination thereof.*

*44. The method of claim 43, wherein said one or more additional active agents are an HMG-CoA reductase inhibitor and aspirin.*

*45. The method of claim 43, wherein said one or more additional active agents are an HMG-CoA reductase inhibitor and a beta blocker.*

*46. A method of producing metformin glycinate comprising the following steps:*

*a) releasing free metformin from metformin hydrochloride by ion-exchange;*

*b) adding glycine to an aqueous liquid comprising the free metformin;*

*c) adding a solvent wherein glycine is insoluble to the aqueous liquid until excess glycine precipitates; and*

*d) removing the precipitated glycine to obtain a liquid comprising said metformin glycinate.*

*47. The method of claim 46, wherein the method further comprises the following steps:*

*concentrating the liquid of b) before c), and*

*e) concentrating the liquid of d) to obtain said metformin glycinate.*

*48. The metformin glycinate prepared by the method of claim 46.*

*49. The metformin glycinate prepared by the method of claim 47.*

* * * * *